United States Patent [19]
Brugger

[11] 3,994,601
[45] Nov. 30, 1976

[54] DYNAMIC CALIBRATION UNIT FOR A TRANSMISSOMETER

[76] Inventor: Richard D. Brugger, 4818 Walker Road, Erie, Pa. 16509

[22] Filed: July 25, 1975

[21] Appl. No.: 599,078

[52] U.S. Cl. ............................ 356/201; 250/227; 250/573; 356/207; 356/243
[51] Int. Cl.² ............... G01N 21/22; G01N 21/12
[58] Field of Search .......... 356/205, 206, 207, 208, 356/243, 201; 350/96 C; 250/227, 564, 565, 573, 575

[56] References Cited
UNITED STATES PATENTS

| | | | |
|---|---|---|---|
| 3,702,734 | 11/1972 | Lindahl et al. | 356/207 |
| 3,838,925 | 10/1974 | Marks | 356/206 |
| 3,850,529 | 11/1974 | Brugger | 356/207 |
| 3,920,980 | 11/1975 | Nath | 250/227 |

Primary Examiner—Vincent P. McGraw

[57] ABSTRACT

A method and apparatus for calibrating a transmissometer having a primary light source and a primary detector for receiving light from the light source through a gas. The apparatus includes a lens supported on a lens. The method and apparatus includes means for catching a beam of light from the primary light source and compressing the beam so that it can be transmitted by a fiber optic guide, then the beam is expanded to its original dimensions so that the normal system sensor sees the source beams at its original dimension.

13 Claims, 15 Drawing Figures

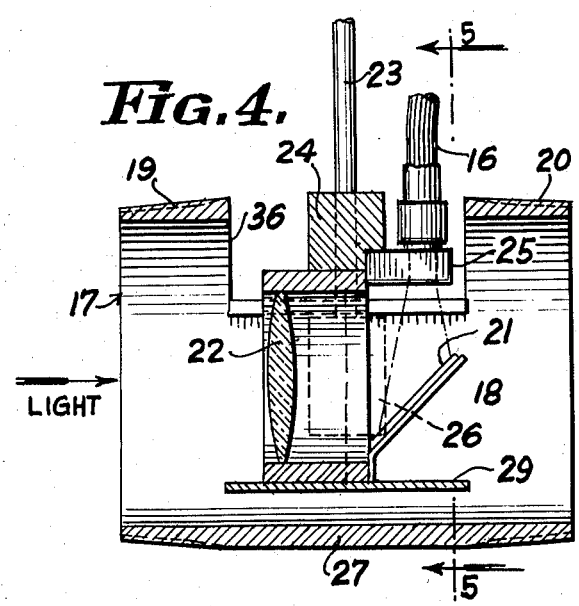
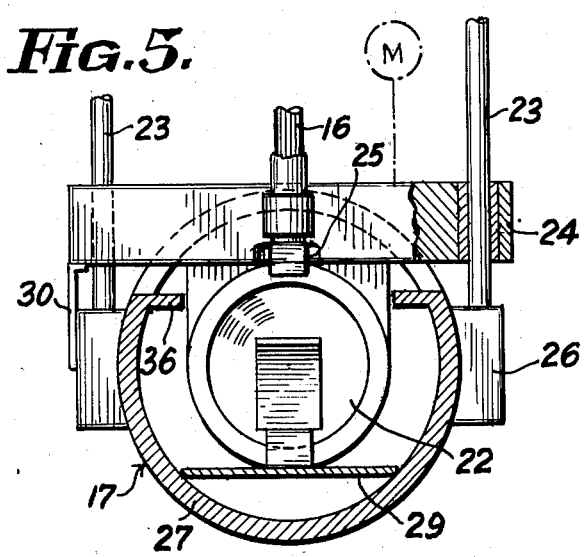
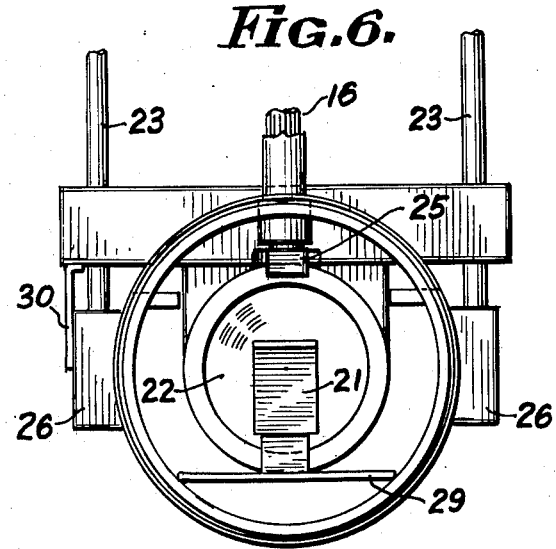
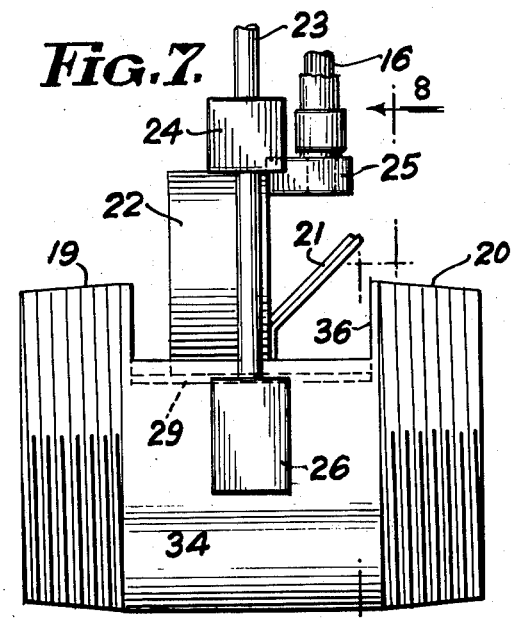
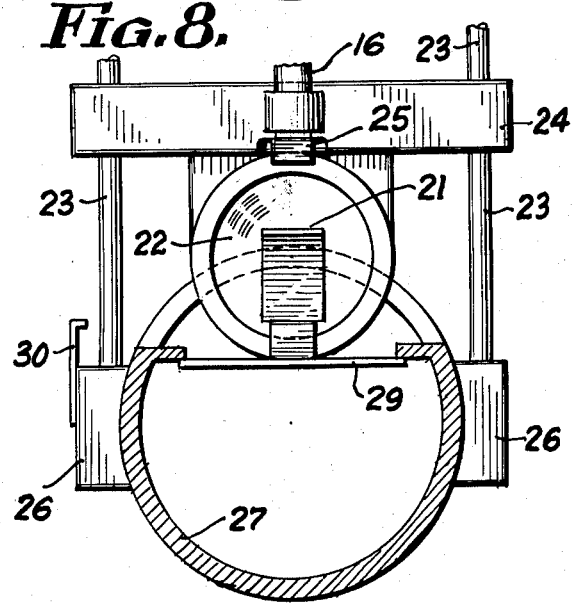
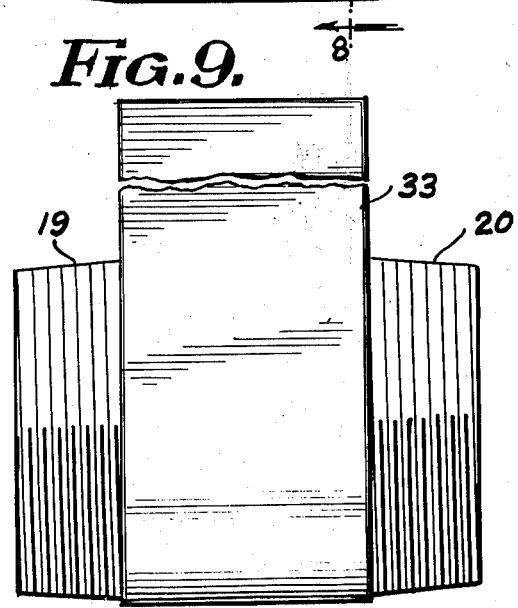

DYNAMIC CALIBRATION UNIT FOR A TRANSMISSOMETER

GENERAL STATEMENT OF INVENTION

The system disclosed has the advantage of simplicity because it has no electrically active parts, except the motors to lower the added optical assemblies into the light pipe.

The mechanism captures the source beam and compresses it to such a dimension that it can be transmitted by a fiber optic guide of reasonable dimension. A bundle up to ¼ inch diameter is reasonable, but a bundle the 2 inches diameter of the beam would be unreasonable. At the exit end of the fiber optic bundle the beam is expanded again to the original dimension so that the normal system sensor "sees" the light beam in its original form, but attenuated by a constant factor. The constant factor depends upon several factors; lens losses, fiber optic bundle end losses, aperture losses, and transmission losses. Transmission losses become a major factor at long range, with the form of $E - XL$ where X is the attenuation constant and L is the length.

The system allows re-zeroing of the transmissometer, compensating for (a) degredation of source lamp intensity, (b) contamination (dirt) on the source window, (c) contamination on the receive window, (d) other system degredation. Furthermore, if the source lamp burns out and is replaced, the transmissometer can be re-zeroed to compensate for the higher level output.

REFERENCE TO PRIOR ART

Dynamic calibration systems of the types disclosed herein are shown in Wager U.S. Pat. No. 3,453,049 and in Brugger U.S. Pat. No. 3,850,529.

OBJECTS OF THE INVENTION

It is an object of the invention to provide an improved method and apparatus for calibrating a transmissometer.

Another object of the invention is to provide a method and apparatus for calibrating a transmissometer that is simple in construction, economical to manufacture and simple and efficient to use.

With the above and other objects in view, the present invention consists of the combination and arrangement of parts hereinafter more fully described, illustrated in the accompanying drawing and more particularly pointed out in the appended claims, it being understood that changes may be made in the form, size, proportion, and minor details of construction without departing from the spirit or sacrificing any of the advantages of the invention.

GENERAL DESCRIPTION OF DRAWINGS

FIG. 4 is a longitudinal cross-sectional view of one of the optical assemblies according to the invention, with the lens tables lowered.

FIG. 5 is a cross sectional view taken on line 5—5 of FIG. 4

FIG. 6 is an end view of the lens table shown in FIGS. 4 and 5.

FIG. 7 is a side view of an optical assembly with the lens table raised.

FIG. 8 is a view similar to FIG. 5 with the lens table raised.

FIG. 9 is a side view of the optical assembly.

DETAILED DESCRIPTION OF DRAWINGS

Figure 1:
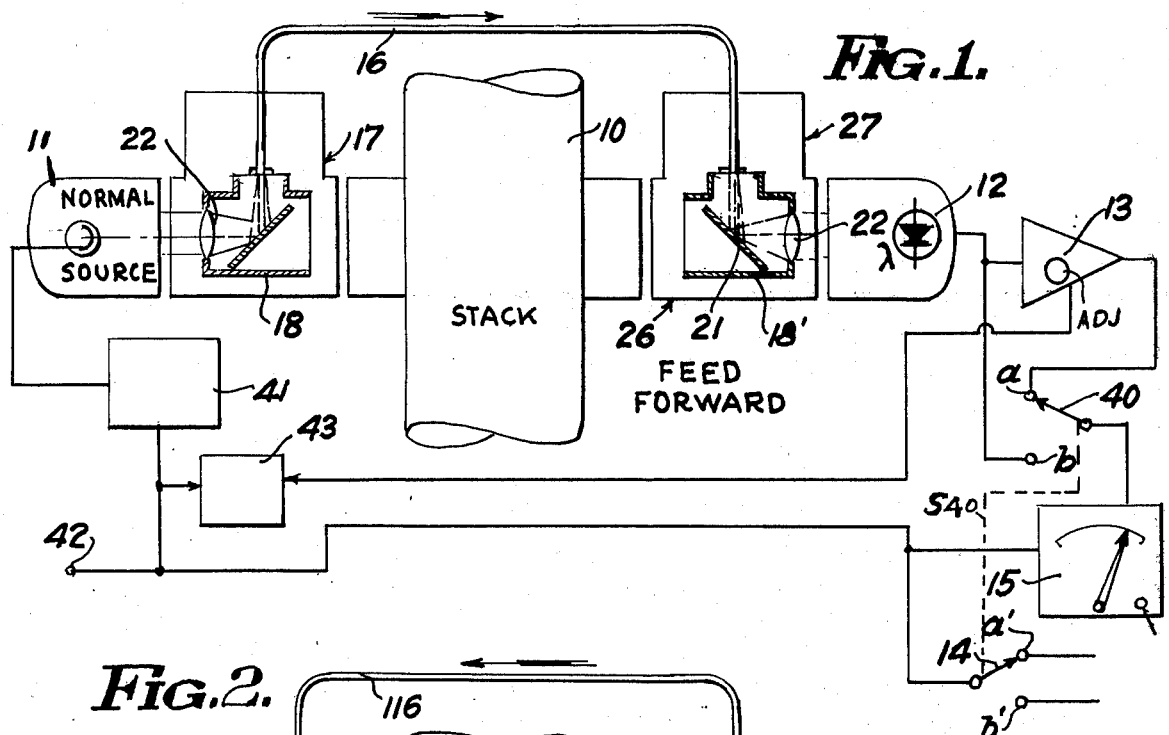
FIG. 1 is a schematic view of the dynamic calibration unit according to the invention showing the lens tables lowered in a position for capturing the light in the feed forward system.

Now with more particular reference to the drawings, the embodiment shown in FIG. 1 shows a smoke stack 10 having a suitable connection at either side to conduct light from the normal light source 11 through the light compression unit 17, through the hollow body of the light expansion unit 27 to the normal sensor 12. The hollow bodies of the light compression unit 17 and the light expansion unit 27 are similar and are shown in greater detail in FIGS. 4-9.

In the embodiment of FIG. 2, and 10 through 15, smoke stack 110 has a primary light path through it as in the embodiment of FIG. 1. A suitable connection is provided at either side to conduct light from the normal source 111 through the light compression unit 117 to the primary sensor 121. Alternatively, when the elevators lower the compression unit 117, light passes through the lens 122, through the attenuator discs 152 onto the mirror 121″ and then on to the auxiliary sensor 150′. At the same time, the elevator carrying the unit 121 is lowered and light from the auxiliary source lamp 121′, is reflected from the concave mirror 121″ on to the primary sensor 112 and light from the auxiliary lamp element 121′ is directed onto the end of the optical fiber bundle 116.

The discs of the attenuating unit 152 are made up of a fixed disc having apertures therein as shown and a rotatable disc can be a lever which can be engaged by the finger of the operator.

Light from the normal source 11 is transmitted to the hollow body of the compression unit 17, through stack 10 and through the hollow body of the expansion unit on to the normal or primary sensor 12. The normal sensor has the pre-amplifier 13 connected to it and to one of the two fixed terminals a and b of the selector switch S40, which is connected to the signal conditioning unit 15. When the lens tables 18 and 18′ are moved up, out of the path of light from the normal source 11, to the normal or primary detector 12, the movable terminal 40 is connected to the conditioning unit 15 and the movable terminal 14 of switch S40 is connected to the AC power input. The ferro-resonant step-down transformer 41, is in turn connected to the normal source 11. The AC power input terminal 42 is connected to the step-down transformer 41 and likewise to the DC power supply 43. The DC power supply is connected to the amplifier 13. The AC power input is likewise connected to the signal conditioning unit 15 and to the movable terminal 14 on the switch S40. Movable terminals 14 and 40 are ganged together as a multi-deck switch S40. The $a'$ terminal of the switch is connected to the elevator lowering motor for lowering the lens tables 18 and 18' into the path of light from the normal source 11 to the normal detector 12. The $b'$ terminal of the switch is connected to the elevator motors to raise or elevate the lens tables 18 and 18' from the path of light from the normal source 11 to the normal detector 12.

Compression unit 17 and the expansion unit 27 each have a generally cylindrical hollow body 34 (shown in detail in FIG. 7), that has lens tables supported therein.

The lens tables 18 and 18' are connected to the ends of the optical fiber bundle 16 by means of connectors 25. The hollow cylindrical body 34 is fixed to the mounting block 26 which has the guide rods 23 fixed thereto and extending upwardly. The bearing bar 24, having bearings 44, is fixed to the lens table and slidably receives the guide rod 23 and is moved up and down by motor M. A mechanical stop 30 is fixed to the mounting block 26 and limits the downward movement of the bearing block so that the lens 22 and mirror 21, fixed to the elevator, are precisely located when in the lowered position.

The cylindrical body 34 has an opening 36 at its top through which the lens table 18 is moved up and down. A closure 29 is supported on the lower side of the lens table. When the lens table is moved to the up position, the closure 29 completely closes the opening 36 against the entrance of dirt, soot, and other contaminants.

The first step in initial set up requires a clear stack and both compression unit 17 and expansion unit 27 retracted. Set the zero on signal conditioner unit 115. Second, lower both compression unit 17 and expansion unit 27 into the light path from 11 to 12. Through successive approximations in alternating between normal source and auxiliary source, adjust the adjustable mechanical attenuator (on source side of stack) until signal conditioner unit 115 reads zero. The foregoing revises the value of $V_s$ until $V_c$ (note that $V_c = V_s$ when loop is balanced) causes auxiliary source 122 to operate at a proper level to cause the signal conditioner unit to read zero. Next, lock the adjustable mechanical attenuator. This completes the set up. Return to normal operation is achieved by retracting both elevators. Dynamic calibration can be accomplished at any subsequent time (even with dense smoke in the stack) by simply (1) turning the dynamic calibration unit switch 51 to position a and pushing the "store" button 53. (note that both elevators are down normal source is on, auxiliary source is off, present value of $V_o$ is stored as $V_s$ in the sample and hold circuit at the instant when "store" button S-3 is pushed.) (2) turn switch 51 to position b (note that elevators are down, normal source is off, auxiliary source to auxiliary sensor, $V_c$ is the present value of $V_o$, control loop forces $V_c = V_s$ — a short time will be required for the control loop to stabilize), (3) adjust the zero adjust on signal conditioner unit 151. (4) return to normal operating condition, switch S1 to position c.

Figure 2:
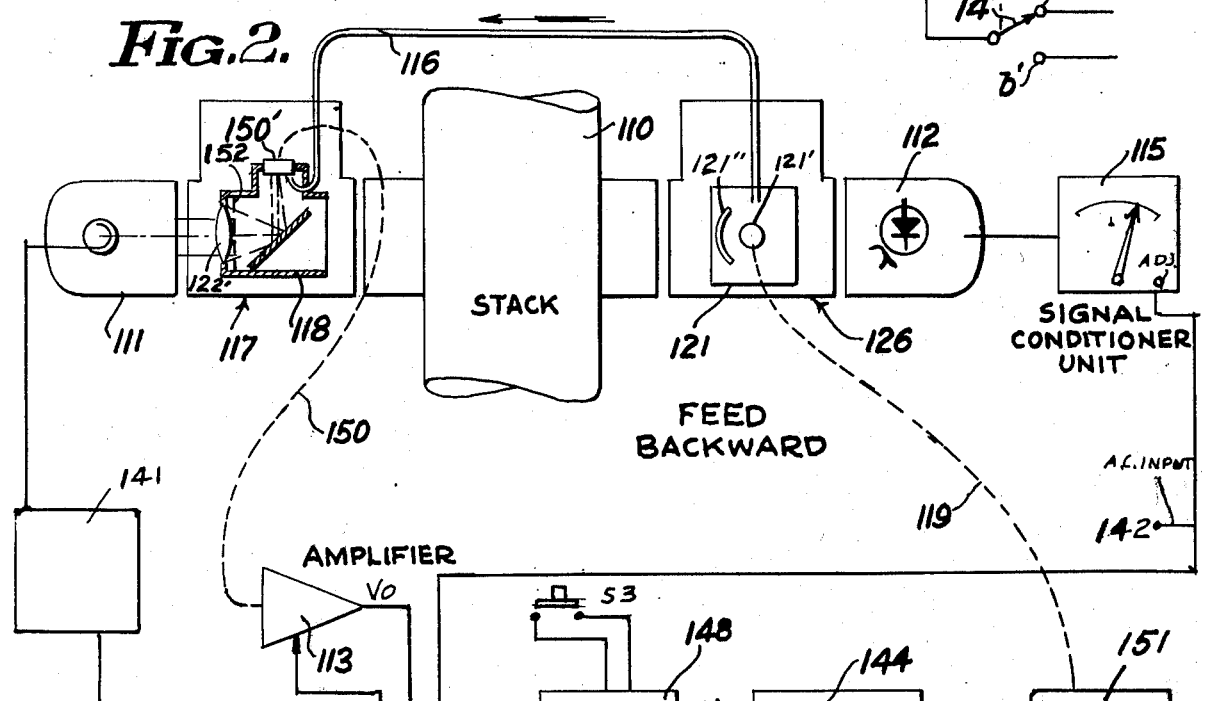
FIG. 2 is a view similar to FIG. 1 of another embodiment of the invention, wherein light is fed back.
Figure 3:
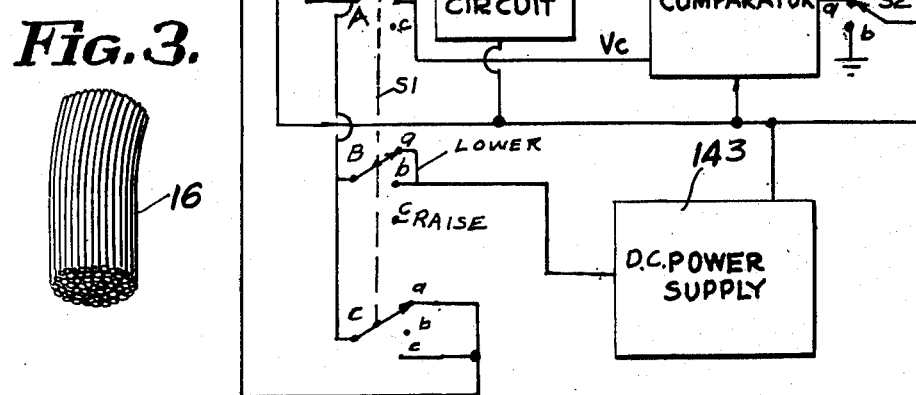
FIG. 3 is a representation of a section of the optical fiber bundle.
Figure 10:
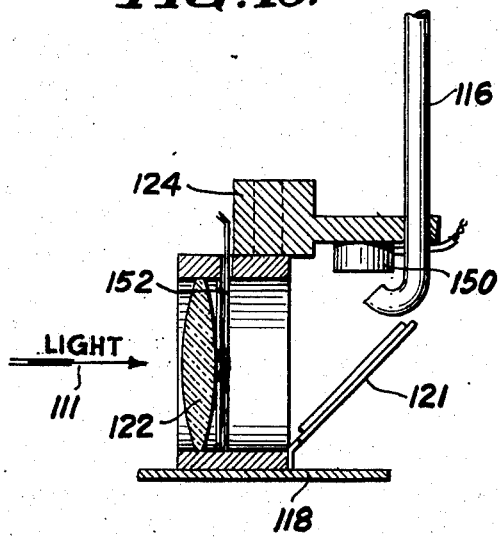
FIG. 10 is a longitudinal cross sectional view of the light compression unit 117 used in the embodiment of FIG. 2 taken on line 10—10 of FIG. 11.
Figure 11:
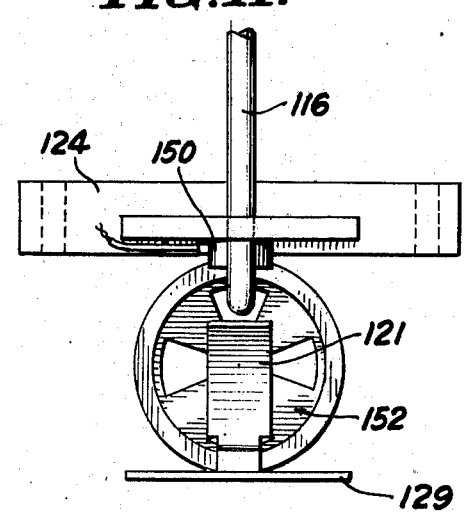
FIG. 11 is an end view, similar to FIG. 6 of the unit shown in FIG. 10.
Figure 12:
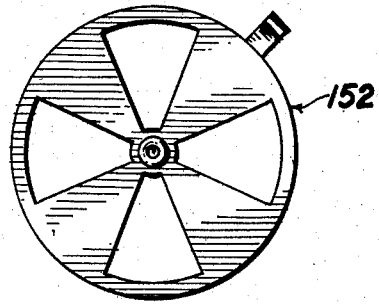
FIG. 12 is an end view of the mechanical attenuator.
Figure 13:
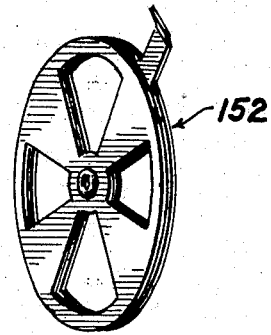
FIG. 13 is an isometric view of the fixed and movable discs of the attenuator shown in FIG. 12.
Figure 14:
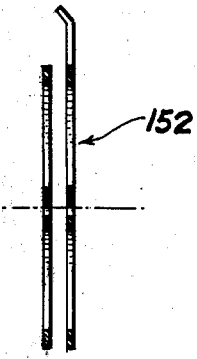
FIG. 14 is a side view of the attenuator shown in FIG. 12.
Figure 15:
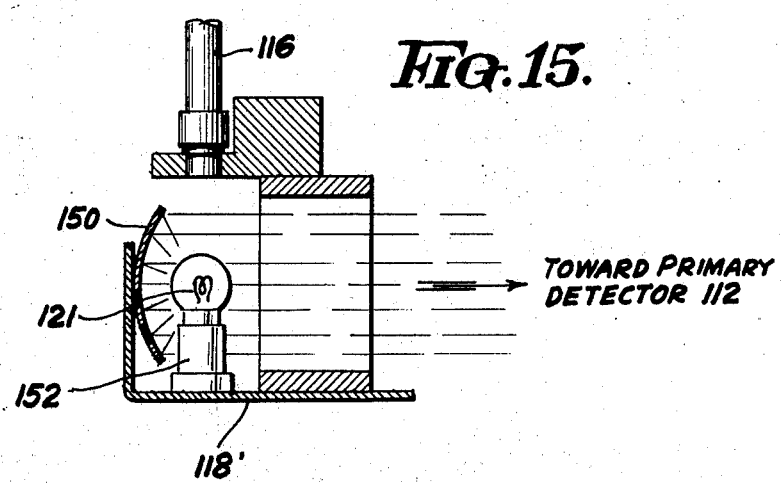
FIG. 15 is a longitudinal cross sectional view of the auxiliary light source with the embodiment shown in FIG. 2.

In the embodiment of the invention shown in FIG. 2, the optical fiber 116 connects the light from auxiliary source 121 to the auxiliary detector 150'. The primary source 111 directs light through the cylindrical body 117, through the stack 110, through the cylindrical body 127, to the primary detector 112, when lens tables 118 and 118' are retracted. The primary detector is connected to signal conditioning unit 115. The auxiliary detector 150' is connected to the amplifier 113 which is in turn connected to the switch S1. Terminal S1-1b carries signal $V_c$ to the comparator 144. Terminal S1-1a is connected to the sample and hold circuit 148 which stores the analog of value of input signal $V_o$ when switch button S3 is pushed. The stored value is called $V_s$ and is in turn connected to the comparator 144. Output of comparator 144 is signal $V_e$, which is the control line into controlled power supply 141.

The output of power supply 141 is connected through line 119 to the auxiliary source 121. The lens table 118 is similar to that shown in the embodiment of FIG. 1; however, the auxiliary detector 150 is substituted for the fiber optic input aperture and an adjustable mechanical attenuator 152 is added. The lens table 121 is similar to the embodiment of FIG. 1 except that the auxiliary source 121' and reflector 121'' replaces the mirror and lens of FIG. 1. Light from auxiliary source 121' is directed into both the primary receiver 112 and into fiber optic bundle 116. Fiber optic bundle 116 carries a sample of the light output of auxiliary source 121' back to auxiliary sensor 150. When auxiliary source 121 is on, normal source 111 is off, and converse, such that auxiliary detector 150' is never excited by both sources simultaneously. Switch S1-2, switches AC power into DC power supply 143 and also to the raise or lower motors which raise or lower the lens tables 118 and 118'. Switch S1-3 switches power into the power supply 141 for energizing primary source 111.

The system requires initial set-up on a clear stack at the time of installation. Recalibration can be performed thereafter, even with dense smoke in the stack.

The embodiment of FIG. 1 is set-up initially by placing switch S40 in the $b$ position, which raises lens tables 18 and 18' and connects the output of detector 12 into the signal conditioner unit 15. Adjust control on signal conditioner unit 15 to reach zero on the scale, then switch S40 is placed in position a which lowers lens tables 18 and 18' and connects the output of detector 12 to signal conditioner unit 15 by way of amplifier 13. Adjust the control on amplifier 13 to give a reading of zero on the signal conditioner unit 15. Switch S40 is returned to position b to return the system to normal operation.

The embodiment of FIG. 1 is re-calibrated by switching S40 to position $a$ and adjusting the control of signal conditioner unit 115 to give zero on the scale. Switching S40 back to $b$ returns the system to normal operation. Re-calibration can be performed at any time, even with smoke in the stack 10.

The embodiment of FIG. 2 is initially set up with a clear stack and switch S1 is in $c$ position, which raises lens tables 118 and 118'. Adjust the control on signal conditioner 115 to give a reading of zero on the meter. Switch S1 to position $b$ and switch S2 to position $b$. This causes lens tables 118' and 118 to be lowered, and the control input to the controlled power supply 151 to be gounded. Adjust control on adjustable power supply 151 to cause signal conditioner 115 to read zero. Switch S2 to position $a$. Alternate between (a) Switch S1 in position $a$ and push S3, and (b) Switch S1 in position $b$ and adjust the adjustable mechanical attenuator 152. Continue to alternate between the two steps until signal conditioner unit 115 is observed to read zero with switch S1 in position $b$ and no further adjustment is required of adjustable mechanical attenuator 152, the mechanical attenuator must then be locked in that position. Switch S1 to normal position c return to normal operation.

The elevator at source side of stack is outfitted with lens 122, auxiliary sensor 150' and the end of the fiber optic bundle 116. The elevator at receiver side of the stack is outfitted with a window, possibly an attenuating window, auxilary source, reflector and the end of the fiber optic bundle.

The auxiliary sensor 150 receives light either from normal source 111 via an adjustable mechanical attenuator or from the auxiliary source via fiber optic bundle 116 but not both at the same time.

Auxiliary source 121 is used only when normal source is turned off, and it puts light (a) into the normal receiver and (b) into fiber optic bundle for transmission to auxiliary sensor.

The embodiment of FIG. 2 is re-calibrated by (a) switch S1 to position a. Press switch S3, (b) switch S1 to position b. Adjust control on signal conditioner unit 115 to cause it to read zero, (c) return S1 to position c to return to normal operation.

The foregoing specification sets forth the invention in its preferred practical forms but the structure shown is capable of modification within a range of equivalents without departing from the invention which is to be understood is broadly novel as is commensurate with the appended claims.

The embodiments of the invention in which an exclusive property or privilege is claimed are defined as follows:

1. An apparatus for calibrating a transmissometer having a primary source of light on a first side of a duct adapted to contain an opaque gas and a primary light sensor on a second side of said duct,
   said primary light source being adapted to provide a beam of light from said primary source of light to said primary light sensor and a normal path through said duct for said normal beam of light,
   and, a meter to indicate opacity,
   and, means to connect said meter to said primary sensor and,
   means to adjust said meter, comprising,
   first optical means on said first side of said duct, moveable into said normal light path,
   second optical means on said second side of said duct, moveable into said normal light path,
   a fiber optic bundle cnnecting said first optical means to said second optical means and disposed in parallel to said normal light path through said duct,
   said optic bundle being adapted to transmit light and provide an optical path between said first and said second optical means,
   said first optical means being adapted to intercept said normal beam of light from said primary source of light and convert said normal beam of light into a spot of light,
   aperture means on said apparatus adapted to receive said spot of light,
   said aperture means being smaller in diameter than the normal beam diameter,
   said second optical means being adapted to reconstitute a beam of light which is geometrically equivalent to the intercepted said normal beam of light.

2. The apparatus recited in claim 1 wherein said second optical means comprises a lens and a mirror,
   said first optical means comprises a lens and a mirror, and, said aperture means comprises the input end of said fiber optic bundle,
   said fiber optic bundle being adapted to transmit light from said first optical means to said second optical means,
   and, said reconstituted beam comprising the light received from said normal source of light as transmitted by said fiber optic bundle, and expanded by said second optical means.

3. The apparatus recited in claim 1 wherein said second optical means comprises a mirror and a lens,
   said mirror is supported to receive light from said fiber optic bundle and,
   said lens is adapted to receive a beam of light from said reflector and to reconstitute said beam of light, and to direct said reconstituted beam of light onto said primary detector.

4. The apparatus recited in claim 1 wherein said first optical means comprises a lens and a mirror and said aperture means comprises an auxiliary light sensor,
   said second optical means comprises a secondary light source and a curved mirror for directing light onto said primary light sensor,
   and, said second optical means comprises means for reconstituting said beam of light,
   said fiber optic bundle being adapted to carry a sample of light from said secondary light source back from said second optical means to said auxiliary light sensor in said first optical means.

5. The apparatus recited in claim 4 wherein said first optical means is adapted to intercept said normal beam of light and convert said normal beam of light into a spot of light,
   and said spot of light is received by said auxiliary light sensor,
   and said sample of light from said secondary light source, as caarried by said fiber optic bundle is received by said auxiliary light sensor,
   means for comparing the two light quantities received by said auxiliary light sensor, but not coincident on said auxiliary light sensor at the same time,
   and means for controlling the intensity of secondary light source such that a proper relationship exists between the intensity of said normal beam of light and said secondary light source.

6. The apparatus recited in claim 1 wherein an auxiliary light sensor is disposed on the first side of said duct,
   and said second optical means comprises a secondary light source, supported on the second side of said duct and,
   one end of said fiber optic bundle is disposed adjacent said secondary light source and a second end of said fiber optic bundle is connected to said auxiliary light sensor, for directing a sample of said light from said auxiliary light source to said auxiliary light sensor.

7. The apparatus recited in claim 1 wherein an auxiliary light sensor is disposed on the first side of said duct,
   and a secondary light source is supported on the second side of said duct and,
   one end of said fiber optic bundle is disposed adjacent said secondary light source and second end of said fiber optic bundle is connected to said auxiliary light sensor, for directing a sample of said light onto said auxiliary light sensor.

8. A method of calibrating a transmissometer made up of a duct, a primary light source and a primary sensor disposed at the opposite side of said duct, a primary light path through said duct,
- moving means for compressing and expanding a light beam into said primary light path,
- said method comprising capturing a beam of light from said primary light source by said means,
- compressing said light to a smaller dimension beam,
- transmitting said smaller dimension beam through a secondary path comprising an optical fiber to a position adjacent said primary sensor,
- expanding said smaller dimension beam to substanially its original dimension,
- and directing said expanded beam of light onto said primary sensor whereby expanded beam is used as the excitor means for said primary sensor for recalibrating said transmissometer.

9. The method recited in claim 8 wherein said beam of light from said primary light source is captured by a lens and directed onto a mirror and from an mirror onto said optic fiber bundle.

10. The method recited in claim 8 wherein said light is received from said optical fiber reflected onto a mirror and directed onto a lens and expanded into a beam of light by said lens and directed onto said primary light sensor.

11. The method recited in claim 10 wherein said means of capturing and expanding said beam of light moves in and out of the path of light from said primary detector.

12. A method of calibrating a transmissometer made up of a duct, a primary light source and a primary sensor disposed at opposite side of said duct, a primary light path through said duct,
- said method comprising capturing a beam of light from said primary light source,
- compressing said beam of light to a smaller dimension beam,
- projecting said smaller dimension beam onto an auxiliary light sensor,
- reconstructing the captured beam at opposite side of duct by means of a secondary light source, so that the reconstructed beam geometry is essentially equal to the original beam geometry,
- sampling the intensity of said secondary light source and relaying that sample back to said auxiliary light sensor,
- comparing the intensities of said smaller dimension beam of light with the sample from said secondary light source,
- and controlling the intensity of said secondary light source so that the comparison shows a proper relationship between the light intensities,
- and using said reconstructed beam in place of the original beam, from said primary source, to calibrate said transmissometer.

13. The method recited in claim 12 wherein said transmissometer is initially calibrated with said primary light path clear of obstruction.

* * * * *